US00PP35346P2

(12) United States Plant Patent
Clark

(10) Patent No.: US PP35,346 P2
(45) Date of Patent: Aug. 22, 2023

(54) ***COLEUS* PLANT NAMED 'UF20-27-11'**

(50) Latin Name: *Coleus scutellarioides*
Varietal Denomination: UF20-27-11

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/803,903

(22) Filed: Jan. 13, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469, 373, 263.1
CPC ..... A01H 5/12; A01H 5/00; A01H 6/50
See application file for complete search history.

(56) References Cited

U.S. PATENT DOCUMENTS

PP27,126 P3 8/2016 Clark et al.
PP35,044 P2 * 3/2023 Clark ..... Plt./469

* cited by examiner

*Primary Examiner* — June Hwu
(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF20-27-11' selected for having a combination of desirable traits that make it well-suited for good performance as an annual plant in the summer landscape. 'UF20-27-11' has novel and contrasting dark red leaf color with prominent chartreuse highlights between the leaf veins and around the leaf margins in a netted pattern. It has very stable leaf color in both sun and shade, is well-branched and vigorous, and maintains its foliage color late into the fall season until frost. 'UF20-27-11' has excellent lateral branching with an upright and spreading growth habit, making it suitable for propagators and producers. It has been observed to have long-season performance in landscape trials.

5 Drawing Sheets

Genus and species: *Coleus scutellarioides*.
Cultivar denomination: 'UF20-27-11'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF20-27-11'. The new cultivar 'UF20-27-11' originated from an open pollination conducted in May-November 2019 in Gainesville, Fla., between the female *Coleus* plant 'UF19-39-10' (unpatented) and an unknown male *Coleus* plant. A single seedling was chosen in May 2020 for further asexual propagation in Gainesville, Fla.

The new cultivar 'UF20-27-11' has been reproduced asexually for over 18 months through vegetative meristem tip cuttings and has been found to retain its distinctive characteristics through successive asexual propagations. 'UF20-27-11' was first propagated asexually by vegetative meristem tip cuttings in May 2020 in Gainesville, Fla., and has remained true-to-type since that time.

Plant Breeder's Rights for the new cultivar 'UF20-27-11' have not been applied for, and 'UF20-27-11' has not been made publicly available more than one year prior to the filing date of this application.

When compared to the female parent, 'UF19-39-10', the new cultivar 'UF20-27-11' has leaves with lobed margins that are broadly acute at the apex, whereas 'UF19-39-10' has leaves with crenate margins and a rounded apex. Additionally, 'UF20-27-11' has dark red colored leaves with prominent chartreuse (yellow green) highlights between the leaf veins and around the leaf margins in a netted pattern, whereas 'UF19-39-10' has predominantly chartreus-colored leaves with maroon mid-veins. 'UF20-27-11' is well-branched plant with excellent lateral branching and a vigorous upright and spreading habit that results in a plant growing wider than it grows tall. 'UF19-39-10' is just as vigorous as 'UF20-27-11', but it has less lateral branching with a more upright habit that results in a plant growing equally as wide as it grows tall.

The new cultivar 'UF20-27-11' was selected because of its vigor, vibrant leaf color, and because of its unique plant habit that fills space laterally in the garden. It performs well in both sun and shade with no change in leaf color. It can withstand the harsh selection conditions plants are subjected to in greenhouse trials and summer farm trials in central Florida. 'UF20-27-11' has not been observed to produce flowers in any trials. Thus, it is an exceptional plant because it maintains its foliage color patterning late into the garden season with minimal plant maintenance (late into the fall season until frost).

SUMMARY OF THE INVENTION

The new cultivar 'UF20-27-11' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF20-27-11' when grown under normal horticultural practices in Gainesville, Fla.: 'UF20-27-11' has the combination of vigorous, upright and spreading growth habit, excellent heat tolerance, and consistent dark red colored leaves with chartreuse highlights between the leaf veins which is significantly different than other *Coleus* plants; it has superior stability in foliage color in both sun and shade conditions, maintaining leaf color under all conditions; it has excellent lateral branching, making it suitable for propagators and producers; and 'UF20-27-11' has been observed to have long-season performance in landscape trials in Gainesville, Fla.

DESCRIPTION OF THE FIGURES

This new *Coleus* cultivar 'UF20-27-11' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar;

FIG. 3 shows a close-up view of the foliage of the new *Coleus* cultivar; and FIG. 4 shows the adaxial side of an immature leaf (left) and a mature leaf (right) of the new *Coleus* cultivar with corresponding R.H.S. color designations; and FIG. 5 shows the abaxial side of an immature leaf (left) and a mature leaf (right) of the new *Coleus* cultivar with corresponding R.H.S. color designations.

DETAILED BOTANICAL DESCRIPTION OF THE CULTIVAR

Figure 1:
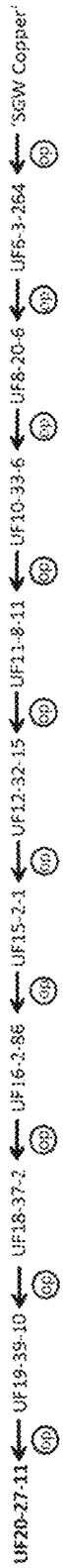
FIG. 1 shows the pedigree of the new *Coleus* cultivar 'UF20-27-11' shown and described herein.
Figure 2:
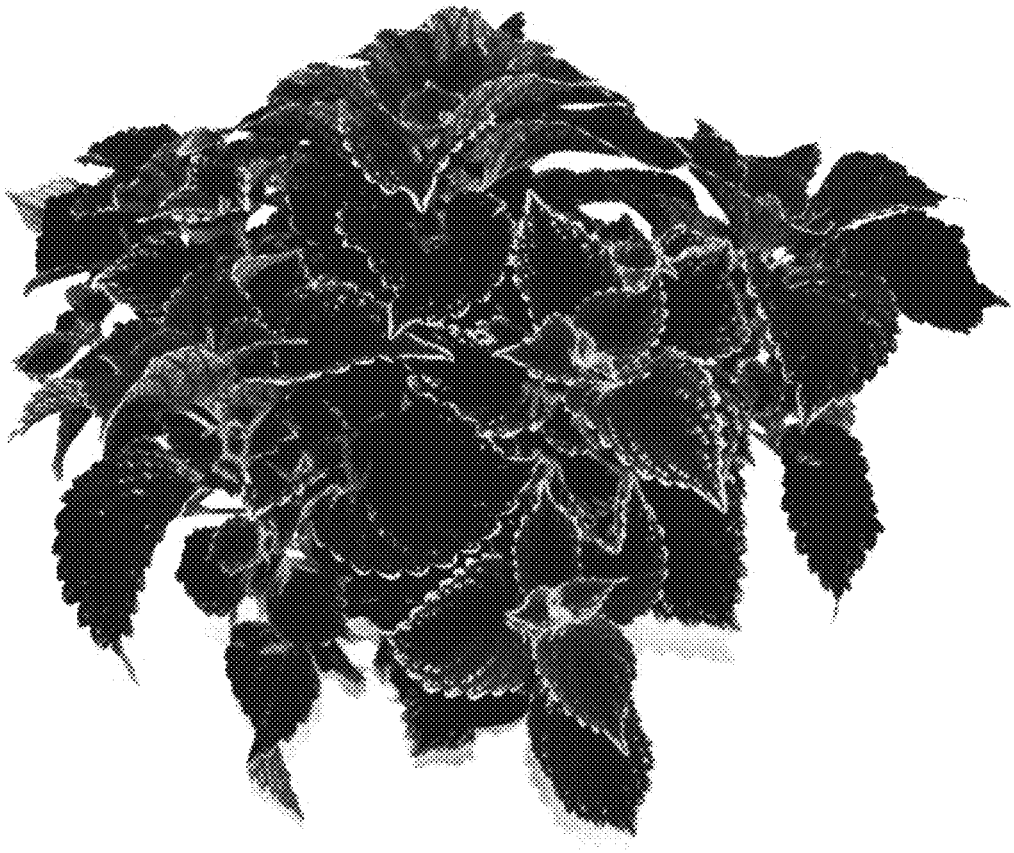
FIG. 2-5 were taken from plants grown ten weeks from unrooted cuttings in February-April 2022 in a glass-covered greenhouse in Gainesville, Fla.
Figure 3:
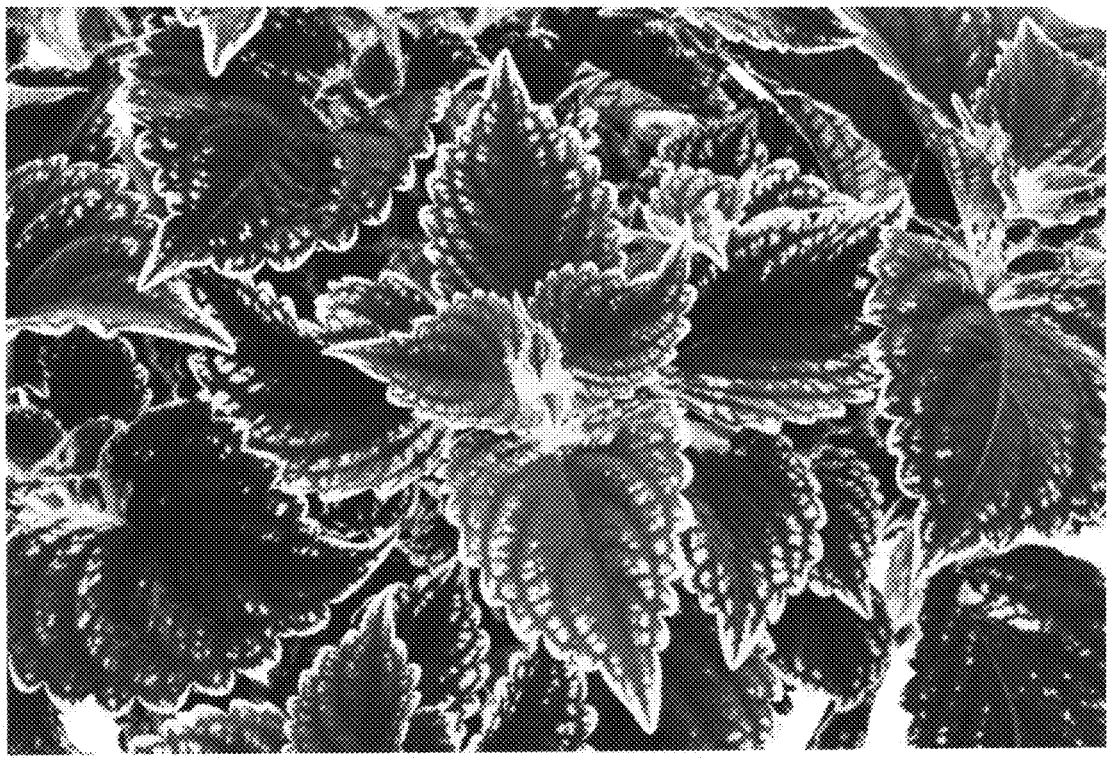
Figure 4:
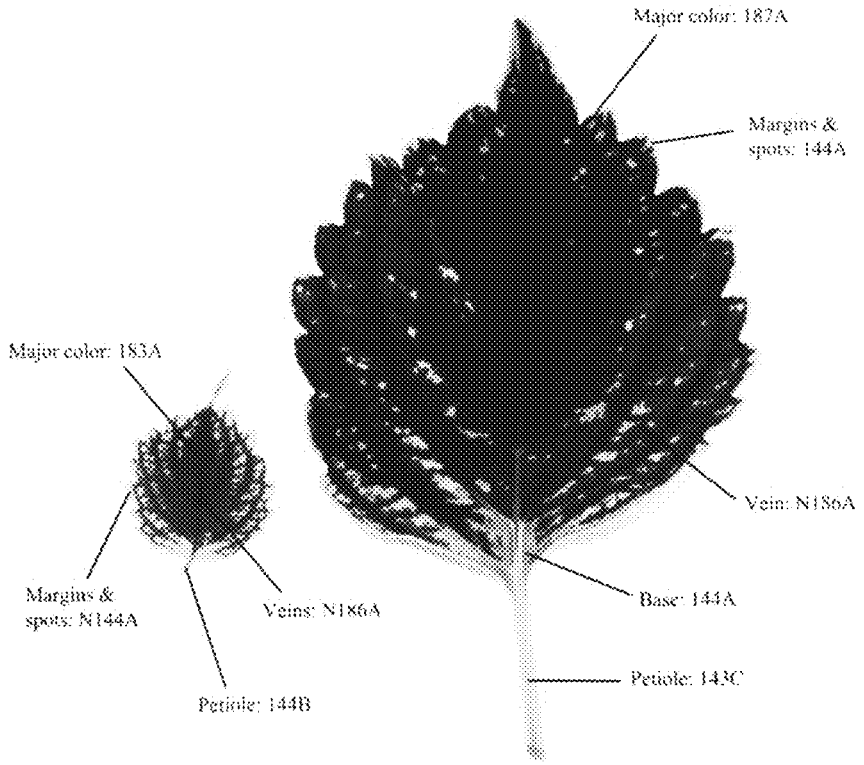
Figure 5:
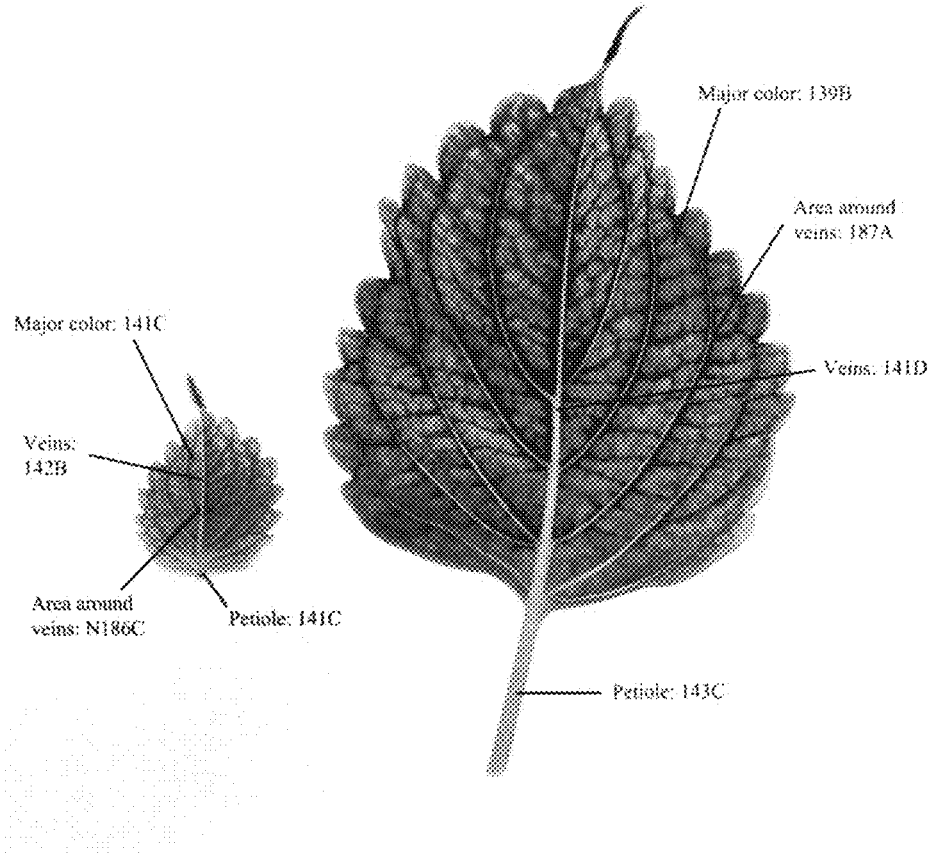

Foliage color was determined under full sun conditions in the middle of the day in a glass-covered greenhouse. Color references are to The R.H.S. Colour Chart of The Royal Horticultural Society of London (R.H.S.), 2007 5th Edition. *Coleus* leaves are rarely one solid color but encompass hues, shades and tints, and color patterns differ from one genotype to another due to varying levels of variegation. The following detailed description of 'UF20-27-11' was obtained using ten-week-old plants grown from unrooted cuttings in February-April 2022 in a glass-covered greenhouse in Gainesville, Fla. The plants were propagated in mist for ten days after cuttings were stuck, then grown in one-gallon pots for approximately eight and a half additional weeks.

BOTANICAL DESCRIPTION

Botanical classification:

*Family*.—Lamiaceae.

*Botanical name*.—*Coleus scutellarioides*.

*Common name*.—*Coleus*.

*Cultivar*.—'UF20-27-11'.

Parentage:

*Female or seed parent*.—'UF19-39-10'.

*Male or pollen parent*.—Unknown.

Propagation:

*Type cuttings*.—Vegetative meristem tip cuttings having at least 1 node.

*Time to initiate roots*.—3-4 days.

*Time to produce a rooted cutting*.—7-10 days.

*Root habit*.—Fibrous.

*Root description*.—Callus forms in 2-3 days, roots initiate in 3-4 days and become a highly branched cutting in 7-10 days.

Plant description:

*Habit*.—Upright and spreading.

*Height* (*from top of soil*).—30-35 cm.

*Width* (*horizontal plant diameter*).—75-80 cm.

Branches:

*Quantity per plant*.—Approximately 12.

*Branch color*.—RHS 141D (yellow green).

*Texture*.—Smooth.

*Pubescence*.—Not present.

*Stem description*.—Square-shaped stem.

*Branch diameter*.—0.9-1.0 cm at the base of a 25-cm-long branch.

*Branch length*.—24-28 cm.

*Internode length*.—3-4 cm measured at mid-branch.

*Anthocyanin*.—Not present.

Leaves:

*Quantity of leaves per branch*.—19-20.

*Arrangement*.—Opposite.

*Fragrance*.—Not fragrant.

*Shape*.—Ovate.

*Length*.—12-14 cm.

*Width*.—11-12 cm.

*Apex*.—Broadly acute.

*Base*.—Attenuate.

*Margin*.—Crenate.

*Leaf texture*.—Upper surface: Pulverulent. Lower surface: Smooth.

*Venation color, mature leaf*.—Upper surface: RHS N186A (purplish grey). Lower surface: RHS 141D (yellow green).

*Venation color, immature leaf*.—Upper surface: RHS N186A (purplish grey). Lower surface: RHS 142B (yellow green).

*Venation pattern*.—Upper surface: Reticulate. Lower surface: Reticulate.

*Color, immature leaf*.—Upper surface, major color: RHS 183A (dark red). Upper surface, edges and spots: RHS N144A (yellowish green). Lower surface, major color: RHS 141C (yellowish green). Lower surface, color around veins: RHS N186C (greyish red).

*Color, mature leaf*.—Upper surface, major color: RHS 187A (dark red). Upper surface, edges and spots: RHS 144A (yellow green). Upper surface, base: RHS 144A (yellow green). Lower surface, major color: RHS 139B (yellowish green). Lower surface, color around veins: RHS 187A (dark red).

*Petiole length*.—5-6 cm.

*Petiole diameter*.—0.3-0.4 cm.

*Petiole color, mature leaf* (*both upper and lower surfaces*).—RHS 143C (yellow green).

*Petiole color, immature leaf.*—Upper surface: RHS 144B (yellow green). Lower surface: RHS 141C (yellowish green).

*Petiole texture.*—Smooth, no pubescence.

Flowers and seeds: Flowers and seeds have not been observed to date during formal trials in Gainesville, Fla.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla., have been long-tailed or citrus mealybugs (*Pseudococcus* spp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

COMPARISON WITH KNOWN CULTIVARS

When the new cultivar 'UF20-27-11' is compared to the commercial cultivar 'UF10-45-12' (U.S. Plant Pat. No. 27,126, commercial name "Coleosaurus"), 'UF20-27-11' has leaves with prominent dark red coloration with some yellow green coloration along the leaf margin and veins colored purplish grey, whereas 'UF10-45-12' has leaves with an equal amount of yellow green and dark red coloration, with the dark red coloration being predominately along the leaf veins.

What is claimed is:

1. A new and distinct *Coleus scutellarioides* plant named 'UF20-27-11' as shown and described herein.

* * * * *